(12) United States Patent
Tuschel et al.

(10) Patent No.: US 7,659,978 B2
(45) Date of Patent: Feb. 9, 2010

(54) PHOTOBLEACHING BY HIGH POWER PULSES

(75) Inventors: David Tuschel, Monroeville, PA (US); Arjun Bangalore, Monroeville, PA (US)

(73) Assignee: ChemImage Corporation, Pittsburgh, PA (US)

( * ) Notice: Subject to any disclaimer, the term of this patent is extended or adjusted under 35 U.S.C. 154(b) by 115 days.

(21) Appl. No.: 11/975,403

(22) Filed: Oct. 19, 2007

(65) Prior Publication Data
US 2008/0094614 A1 Apr. 24, 2008

Related U.S. Application Data

(60) Provisional application No. 60/852,766, filed on Oct. 19, 2006.

(51) Int. Cl.
*G01N 21/65* (2006.01)
*G01N 1/00* (2006.01)
(52) U.S. Cl. .......................... 356/301; 356/36
(58) Field of Classification Search ................ 356/36, 356/301
See application file for complete search history.

(56) References Cited

U.S. PATENT DOCUMENTS

| 2005/0010091 A1* | 1/2005 | Woods et al. ............... 600/316 |
| 2006/0092414 A1 | 5/2006 | Geshwind et al. |
| 2006/0200013 A1 | 9/2006 | Smith et al. |
| 2006/0203238 A1 | 9/2006 | Gardner et al. |

OTHER PUBLICATIONS

MacDonald et al., On the Use of Photobleaching to reduce Fluorescence Background in Raman Spectroscopy to Improve the Reliability of Pigment Identification on Painted Textiles, J. Raman Spec., vol. 37, p. 830-835 (Aug. 2006).
Rosch et al., Chemotaxonomic Identification of Single Bacteria by Micro-Raman Spectroscopy: Application to Clean-Room Relevant Biological Contaminations, Appl. Env. Microbiol., vol. 71, No. 3, p. 1626-1637 (Mar. 2005).

* cited by examiner

*Primary Examiner*—F. L Evans
(74) *Attorney, Agent, or Firm*—Morgan Lewis & Bockius (57) ABSTRACT

A pulse photobleaching methodology wherein a monochromatic illumination (e.g., laser illumination) having a higher power intensity (photobleaching power) just below the photodamage threshold of a luminescent sample is initially used to significantly attenuate sample luminescence without photothermally destroying the sample material. Thereafter, the laser power density may be reduced to a significantly lower level (analytical power level) to carry out spectroscopic measurements (e.g., collection of Raman scattered photons) on the sample. In one embodiment, the laser illumination wavelength remains the same despite changes in laser power intensity. Some figures-of-merit may be computed from optical measurements made at the analytical power level to guide the photobleaching process. Sample-dependent combinations of laser power density and short exposure times may be obtained to significantly expedite photobleaching to assist in collection of sample spectral data in the field without a long wait. Portable spectroscopy systems employing pulse photobleaching may be devised for expeditious collection of spectral data from luminescent samples in the field.

16 Claims, 8 Drawing Sheets

PHOTOBLEACHING BY HIGH POWER PULSES

REFERENCE TO RELATED APPLICATION

The disclosure in the present application claims priority benefit of the U.S. Provisional Application No. 60/852,766, titled "Photobleaching by High Power Pulses," and filed on Oct. 19, 2006.

BACKGROUND

1. Field of the Disclosure

The present disclosure generally relates to photobleaching of luminescent materials and, more particularly, to a system and method of photobleaching using a fixed-wavelength, variable intensity laser illumination.

2. Brief Description of Related Art

Raman spectroscopy may be used for the identification of biological and chemical materials. A significant impediment to the acquisition of Raman spectra, particularly of samples of biological materials or industrial chemical mixtures/solutions, is the luminescence in the sample generated by the illumination used to generate the Raman scattering. This occurs when any or all of the material components being illuminated absorb light at the monochromatic wavelengths used to generate spontaneous Raman scattering. Once the material has achieved an excited electronic state through such absorption, emission (luminescence) over a broad range of wavelengths may occur. Because absorption and luminescence have a much higher overlap integral or cross-section (over the material surface) than does Raman scattering, the luminescence can often partially, if not totally, obscure the Raman scattered photons.

To overcome the problem of luminescence without resort to changing the excitation wavelengths, those skilled in the art have used a practice known as photobleaching. The method of photobleaching involves first bathing the sample in the laser light at the same wavelength and power to be used for the subsequent acquisition of Raman spectra. The principal result of this photobleaching is that the emission strength of the luminescence is significantly attenuated relative to that observed upon initial illumination. Furthermore, the emission strength of luminescence has been attenuated sufficient for the detection of Raman scattered photons. The duration of photobleaching required under these conditions can range from tens of minutes to several hours. Because of growing usage of Raman spectra in detection of biological and chemical threat agents in the field, it is desirable to expedite photobleaching and Raman detection processes so that decisions can be made quickly in the field (as opposed to a controlled, laboratory environment) without a long wait. It is therefore desirable to devise a photobleaching methodology that is significantly faster than the prior art approach.

SUMMARY

In one embodiment, the present disclosure relates to a method that comprises the step of photobleaching a sample by applying a monochromatic illumination at a first intensity level to the sample for a first duration, wherein the first intensity level is slightly lower than a photodamage threshold of the sample. The method also comprises the step of reducing intensity of the illumination from the first intensity level to a second intensity level without changing wavelength of the illumination, wherein the second intensity level is substantially lower than the first intensity level. The method further includes the step of applying the illumination at the second intensity level to the sample for a second duration so as to measure an optical response of the sample.

In another embodiment, the present disclosure relates to a system comprising a sample; and an excitation source configured to illuminate the sample using monochromatic light. The excitation source is configured to provide: (i) a first illumination having a first intensity level and configured to be applied to the sample for a first duration so as to photobleach the sample, wherein the first intensity level is slightly lower than a photodamage threshold of the sample, and (ii) a second illumination identical in wavelength to the first illumination and having a second intensity level, wherein the second intensity level is substantially lower than the first intensity level, and wherein the second illumination is configured to be applied to the sample after the first illumination for a second duration so as to measure an optical response of the sample.

In a further embodiment, the present disclosure relates to a system, which comprises means for applying a laser illumination to a luminescent sample at a first intensity level and for a first duration so as to photobleach the sample, wherein the first intensity level is slightly lower than a photodamage threshold of the sample; means for applying the laser illumination to the sample at a second intensity level and for a second duration after the first duration without changing wavelength of the illumination, wherein the second intensity level is substantially lower than the first intensity level; and means for measuring a spectral response of the sample when the laser illumination is applied to the sample at the second intensity level.

The present disclosure describes various embodiments of a pulse photobleaching methodology wherein a monochromatic illumination (e.g., laser illumination) having a higher power intensity (photobleaching power) just below the photodamage threshold of a luminescent sample is initially used to significantly attenuate sample luminescence without photothermally destroying the sample material. Thereafter, the laser power density may be reduced to a significantly lower level (analytical power level) to carry out spectroscopic measurements (e.g., collection of Raman scattered photons) on the sample. In one embodiment, the laser illumination wavelength remains the same despite changes in laser power intensity. Some figures-of-merit may be computed from optical measurements made at the analytical power level to guide the photobleaching process. Sample-dependent combinations of laser power density and short exposure times may be obtained to significantly expedite photobleaching to assist in collection of sample spectral data in the field without a long wait. Portable spectroscopy systems employing pulse photobleaching may be devised for expeditious collection of spectral data from luminescent samples in the field.

BRIEF DESCRIPTION OF THE DRAWINGS

For the present disclosure to be easily understood and readily practiced, the present disclosure will now be described for purposes of illustration and not limitation, in connection with the following figures, wherein.

DETAILED DESCRIPTION

The accompanying figures and the description that follows set forth the present disclosure in embodiments of the present disclosure. However, it is contemplated that persons generally familiar with spectral measurements, operation and maintenance of optical instruments (including spectroscopic instruments), or optical spectroscopy will be able to apply the teachings of the present disclosure in other contexts by modification of certain details. Accordingly, the figures and description are not to be taken as restrictive of the scope of the present disclosure, but are to be understood as broad and general teachings. In the discussion herein, when any numerical range of values is referred or suggested, such range is understood to include each and every member and/or fraction between the stated range of minimum and maximum.

In the photobleaching approach according to one embodiment of the present disclosure, a higher laser power illumination (than that used for routine spectral data acquisition such as, Raman data collection) occurs over a period of seconds to several minutes at a maximum illumination intensity level such that the luminescence has been attenuated sufficient for the subsequent detection of Raman scattered photons. Thus, in one embodiment of the present disclosure, the laser illumination wavelength remains the same during photobleaching and Raman detection. However, the laser signal power density or intensity is varied depending on the phase in progress—photobleaching or Raman detection. In one embodiment, this targeted dual-intensity approach may be called "pulse photobleaching". In practice, it may be desirable to find a practical, if not the optimal, combination of laser power density and short exposure time such that the emission strength of the sample luminescence has been attenuated sufficiently without photothermally destroying the sample material. Clearly, the necessary conditions will be material-dependent, and, hence, additional experiments may be performed on power intensity and timing strategies to achieve the best results for different classes of materials. Some experimentally obtained results using the pulse photobleaching approach discussed herein are discussed later hereinbelow with reference to FIGS. 3-7.

It is noted here that in the discussion below, the term "fluorescence" is sometimes used interchangeably with the broader term "luminescence." However, it is apparent to one skilled in the art "fluorescence" is a specie of the genus "luminescence" and, hence, the teachings of the present disclosure are contemplated to be equally applicable in case of pulse photobleaching of sample luminescence as well as sample fluorescence. Furthermore, the terms "power intensity" and "power density" may be construed to be synonymous in the discussion hereinbelow.

Figure 1A:
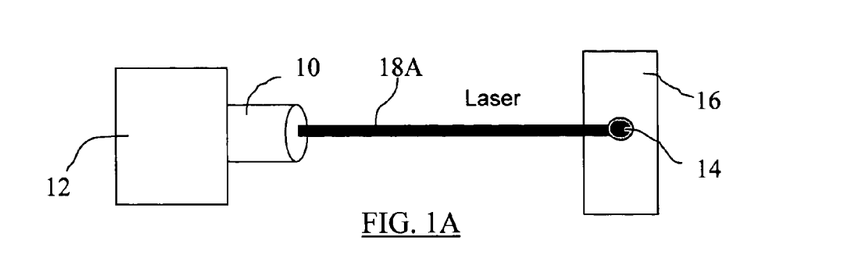
FIGS. 1A and 1B provide an exemplary illustration of a dual-intensity pulse photobleaching application according to one embodiment of the present disclosure.
Figure 1B:
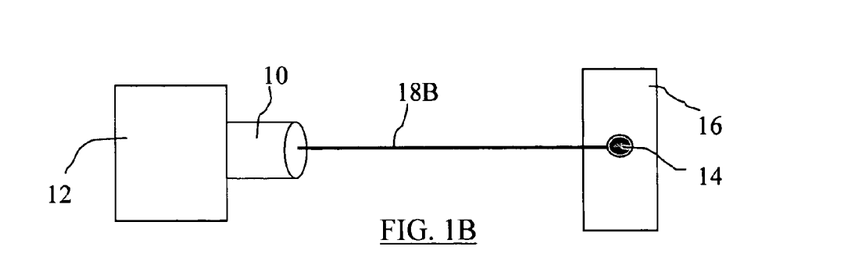

FIGS. 1A and 1B provide an exemplary illustration of a dual-intensity pulse photobleaching application according to one embodiment of the present disclosure. FIG. 1A illustrates a TEC-cooled (thermo-electrically cooled) laser head 10 (with TEC cooling mechanism 12) illuminating a portion of a dried sample 14 that is placed on an AL (aluminum) slide 16 during a photobleaching phase according to one embodiment of the present disclosure. The laser head 10 may provide monochromatic illumination of a predetermined wavelength. In FIG. 1A, the higher intensity of the laser illumination is represented (for illustrative purpose only) by the thickness of the laser beam 18A. After photobleaching, the laser intensity is reduced (as represented by a thinner laser beam 18B in the illustration of FIG. 1B) to carry out spectroscopic measurements (e.g., Raman detection). However, as mentioned before, the wavelength of laser illumination in the embodiments of FIGS. 1A and 1B remains the same.

It is noted here that the optical path and beam diameter of a laser beam (e.g., the laser beam 18A) for photobleaching may not be the same as the optical path and beam diameter of the laser beam (e.g., the laser beam 18B) for Raman data acquisition. For example, as discussed later hereinbelow with reference to FIG. 9, the photobleaching may be performed using laser illumination that is at an oblique angle to a sample plane of reference (e.g., horizontal), whereas laser illumination to collect Raman-scattered photons may be at a different angle (e.g., vertical) from the sample reference plane. In an alternative embodiment (not shown herein), the photobleaching light and laser illumination for Raman scattering may both be at oblique angles with respect to a sample plane of reference.

Figure 2:
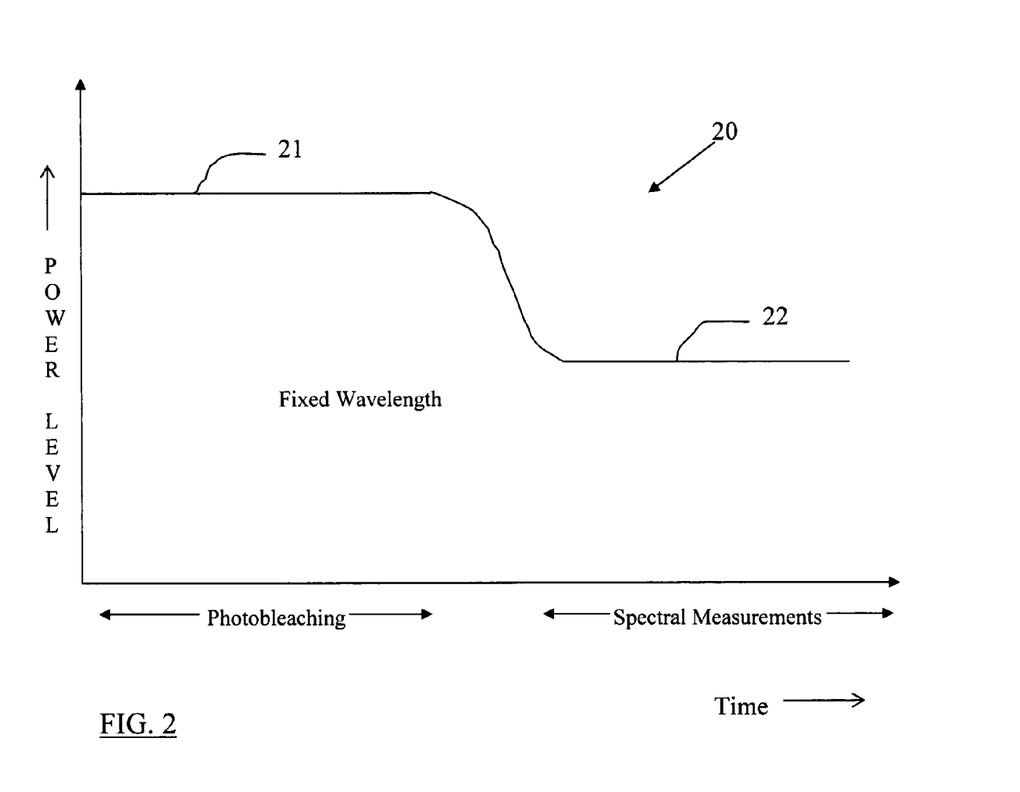
FIG. 2 illustrates an exemplary plot of a dual-intensity laser illumination for pulse photobleaching according to one embodiment of the present disclosure.

FIG. 2 illustrates an exemplary plot 20 of a dual-intensity laser illumination for pulse photobleaching according to one embodiment of the present disclosure. FIG. 2 illustrates exemplary CW (continuous wave) laser output power levels 21-22 depicting the reduction in output power level from a higher level 21 to a substantially lower level 22 (without any change in the laser illumination wavelength) when switching from photobleaching to Raman detection according to the teachings of one embodiment of the present disclosure. In one embodiment, a software-controlled CW laser (e.g., a MicroGreen™ series 532 nm laser marketed by Snake Creek Lasers of Hallstead, Pa., USA) may be employed to switch the intensity (amplitude) of the laser output signal from higher power/intensity (during photobleaching) to lower power/intensity (during, for example, Raman spectroscopy) under software control. In an alternative embodiment, instead of a software-controlled laser, a fixed intensity (or power level) CW laser may be used in conjunction with a neutral-density filter. In such an embodiment, to accomplish the desired switching of the laser output power level, the neutral-density filter (not shown) may be placed or slid in/out in front of the laser output using a lever (not shown). Such switchable-filter design may be preferred when mechanically feasible (on the instrument carrying the laser) and when it is not desired to invest in a higher cost, software-controlled dual-intensity laser.

It is noted here that the teachings of the present disclosure may be implemented in any monochromatic illumination-based (e.g., laser-based) photobleaching application, whether as part of optical or chemical imaging/spectroscopy, or just as a stand-alone photobleaching application. Some examples of luminescent materials that can be photobleached in the manner discussed herein include chemical (natural or synthetic) and biological luminescent materials where luminescence may be naturally-occurring or artificially-induced. Results of photobleaching of two of such materials—MCC (Micro Crystalline Cellulose) and Bg (*Bacillus globigii*)—carried out according to the teachings of the present disclosure are discussed later hereinbelow with reference to FIGS. 3-7.

Prior to carrying out photobleaching of a sample, it may be desirable to either determine the photodamage threshold of the sample (using a portion of the sample or a sample similar to the sample under investigation) or use a pre-determined value for such threshold. In one embodiment, photodamage thresholds for some standard samples (e.g., Bg, Bt (*Bacillus Thuringiensis*), MCC) may be pre-determined and stored in the memory of the instrument that will be used to carry out the pulse photobleaching according to the teachings of the present disclosure. Such pre-stored values may obviate the need to determine them in the field, thereby reducing the time needed for pulse photobleaching. Using the photodamage threshold value (whether pre-determined or determined at run time), a sample may be photobleached in the following manner according to one embodiment of the present disclosure:

(1) Initially, the laser power output may be set to a higher level that is substantially close to or just below the photodamage threshold of the sample. This power may be referred to herein as the "photobleaching power" (the photobleaching power level is indicated by reference numeral "21" in the exemplary plot 20 in FIG. 2). The sample (e.g., on a substrate or in the form of a pile of powder) then may be photobleached for a fixed time (varies from a few seconds to a few minutes) at this photobleaching power level. The duration of photobleaching may be pre-determined (e.g., based on the data available for the sample to be examined) or may be determined at run-time (e.g., based on the sample under investigation in the field).

(2) After the initial photobleaching in step (1), the laser power output may be reduced to a lower level referred to herein as the "analytical power" level (indicated by reference numeral "22" in the exemplary plot 20 in FIG. 2 and discussed in more detail hereinbelow) and sample's optical response measurement may be made at this analytical power level. In one embodiment, the optical response measurement may include collection of a Raman spectrum of the sample. In another embodiment, the optical response measurement may include collection of a fluorescence spectrum. In a further embodiment, one or more figures-of-merit (FOM) may be computed from the optical response measurement to guide the photobleaching process. The FOM's may include, for example: (i) Total Intensity (or Sum of Squares)—The Total Intensity FOM may be computed by calculating the total intensity of all the points on the fluorescence spectrum obtained through the immediately preceding optical response measurement. Instead of computing the total intensity, the Sum of Squares approach computes the sum of squares of intensity values of all or a selected group of points in the fluorescence spectrum. (ii) No Saturation (e.g., in the fluorescence spectral plot)—This FOM relates to observing the fluorescence spectrum (obtained in an immediately preceding optical response measurement) to identify whether there are any intensity values in the spectrum that are equal to the saturation limit of a detector (e.g., a CCD detector) used to collect the fluorescence spectrum data. An absence of intensity values at the CCD saturation level may indicate a favorable photobleaching status of the sample (i.e., the sample may have been sufficiently photobleached). (iii) Appearance of a CH Peak—This FOM may relate to photobleaching of biological samples (e.g., Bg or Bt). A presence of a CH (Carbon-Hydrogen) peak in the fluorescence spectrum (obtained in an immediately preceding optical response measurement) of the biological sample under investigation may indicate a favorable photobleaching status of the sample (i.e., the sample may have been sufficiently photobleached). (iv) Percentage Change in Total Intensity—This FOM computes percentage change in the Total Intensity FOM between two successive process iterations.

(3) Then, the photobleaching mentioned in step (1) may be performed again, followed by the optical response measurement and FOM computation of step (2). During such iterations, if the most-recently computed FOM has not changed significantly from the FOM computed in the immediately preceding iteration (i.e., when a reasonable stabilization in FOM values has been observed), the sample may be considered to have become photobleached. Otherwise, it may be desirable to go back to step (1) and repeat the measurement cycle (to measure optical response and computer FOM as indicated in step (2)) until the FOM's associated with two most-recent successive iterations do not change significantly. In one embodiment, two successive FOM's may be considered not to have changed significantly when their values are within 2% to 5% above any readout variation attributed to an optical detector (e.g., a CCD) used during the optical response measurements.

Some applications of pulse photobleaching according to one embodiment of the present disclosure may include photobleaching of MCC and Bg as discussed herein with reference to the experimental results depicted in FIGS. 3-7. Other applications may include photobleaching of commercially available polymers, stock chemicals, fabricated materials, etc.

Figure 3A:
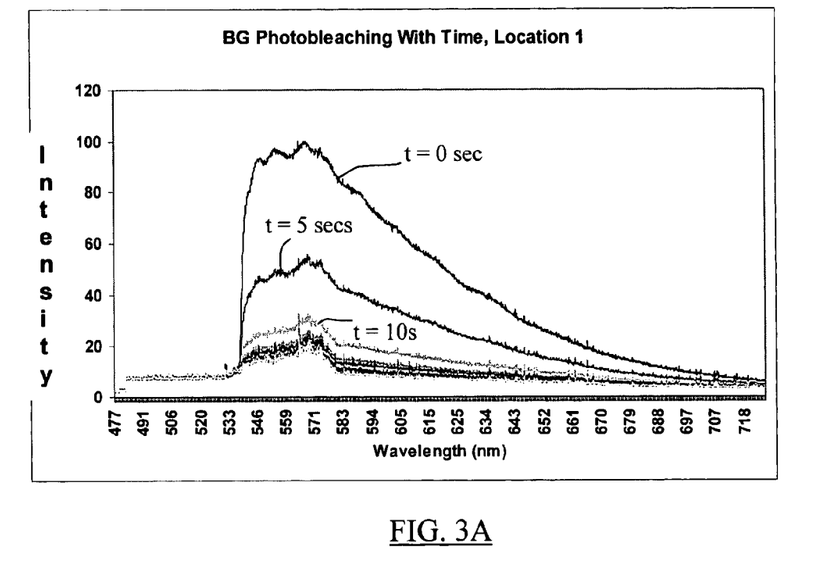
FIGS. 3A, 3B, 4A and 4B depict exemplary fluorescence and photobleaching plots for two representative spatial locations on a Bg sample.
Figure 3B:
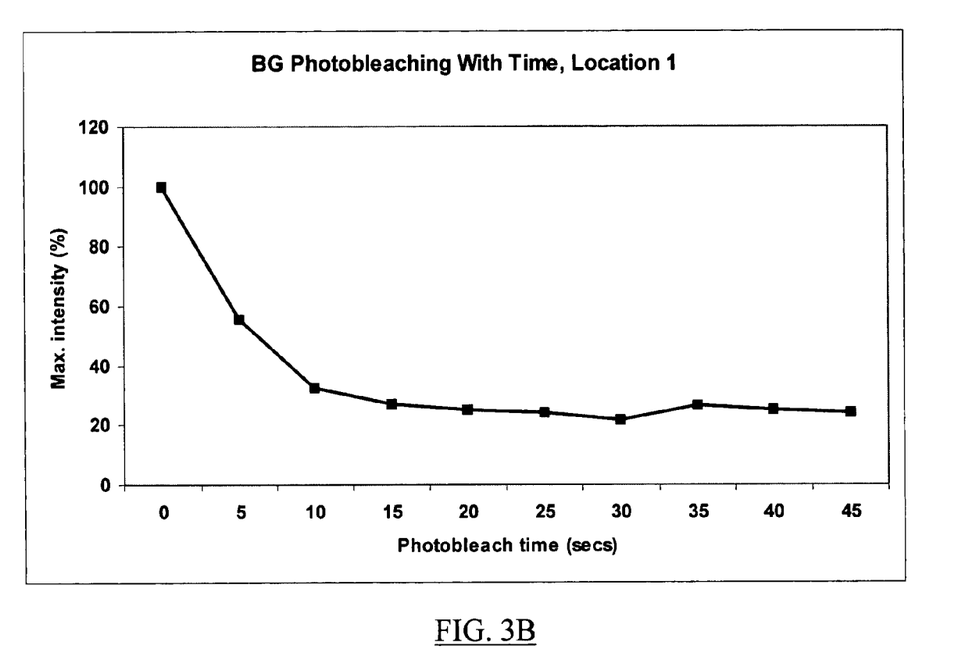
Figure 4A:
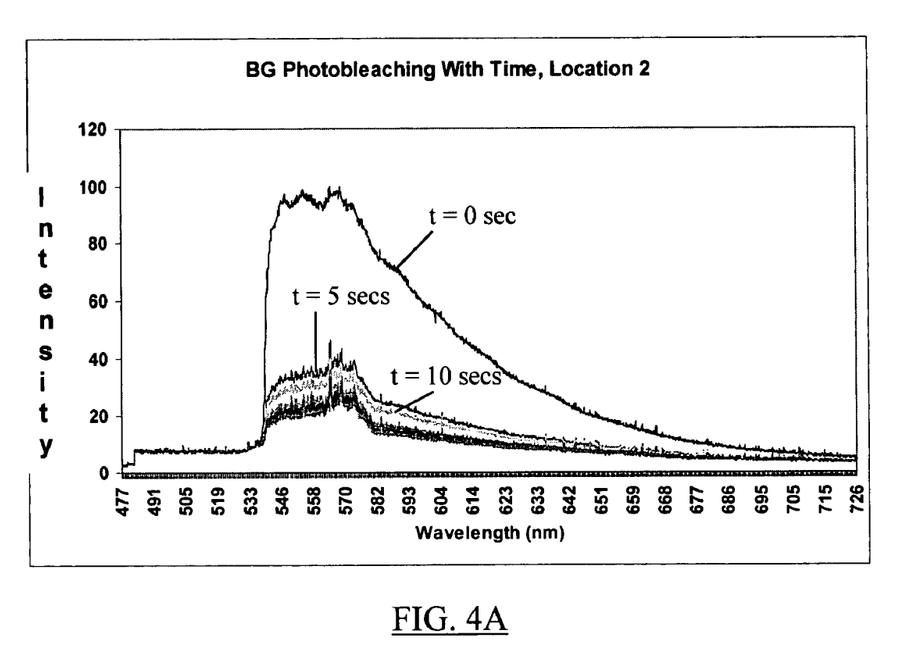

FIGS. 3A, 3B, 4A and 4B depict exemplary fluorescence and photobleaching plots for two representative spatial locations (indicated as "Location 1" and "Location 2" in FIGS. 3 and 4) on a Bg sample. The plots in FIGS. 3A and 4A illustrate variations in fluorescence with time for respective Bg locations. Thus, the fluorescence decay waveforms in FIG. 3A relate to fluorescence observed from Bg location-1 at various times during photobleaching (at photobleaching power level) of location-1 according to the teachings of one embodiment of the present disclosure. Similarly, the fluorescence waveforms in FIG. 4A relate to fluorescence observed from Bg location-2 at various times during photobleaching. Some exemplary time values indicated on the plots in FIGS. 3A and 4A correspond to the photobleach time (in seconds) represented on the x-axis in plots in FIGS. 3B and 4B, respectively.

As noted below with reference to FIG. 5, the Bg sample had spatially varying fluorescence and, hence, the photobleaching rates were different for the same amount of photobleaching for the two sample locations in FIGS. 3 and 4. For example, in the embodiment of FIG. 3B, the fluorescence was reduced to about 30% of its initial value in just about 10 seconds of photobleaching at about 80 mW (with 814 mA current) of photobleaching power. On the other hand, it took about 30 seconds to photobleach the location-2 in the embodiment of FIG. 4B to 30% of its initial fluorescence value with the same laser power (approximately 80 mW) as in case of the location-1 in FIG. 3B. With all photobleaching parameters (e.g., laser power, power stabilization time, etc.) being equal in the embodiments in FIGS. 3 and 4, it is seen from FIG. 4B that the fluorescence reduces to just about 40% of its initial value in approximately 10 seconds of photobleaching (whereas it reduced to about 30% of its initial value in case of the Bg location-1 in FIG. 3B).

Figure 4B:
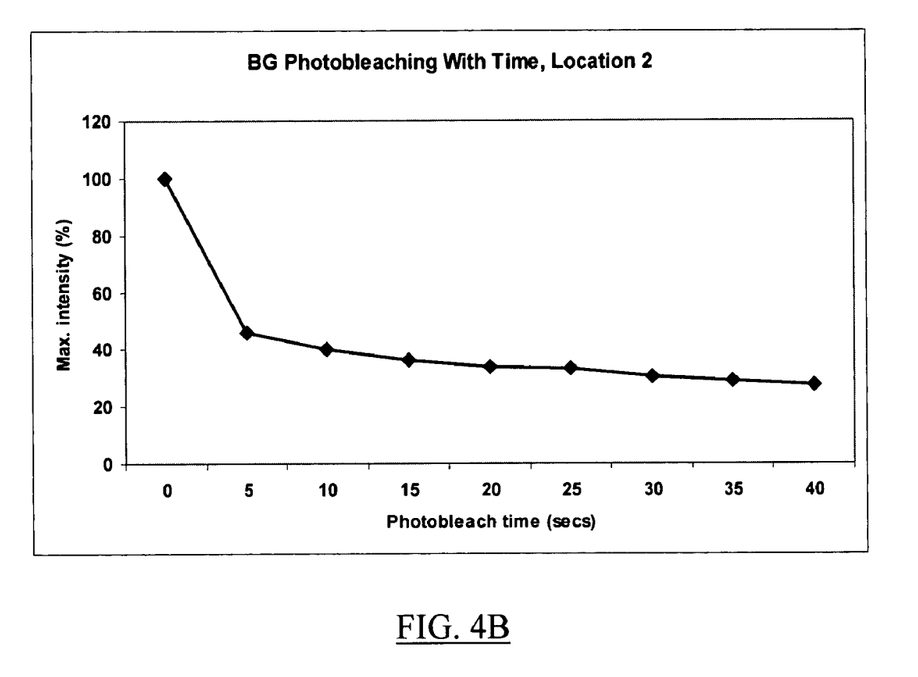
Figure 10:
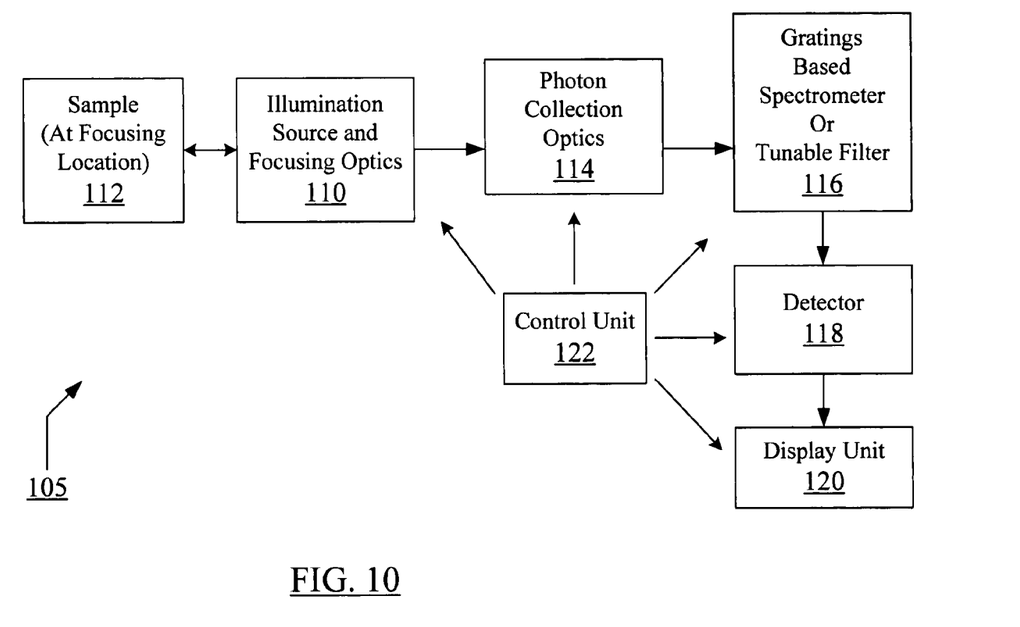
FIG. 10 depicts an exemplary compact Raman and/or fluorescence spectroscopy system for portable or handheld spectroscopy applications according to one embodiment of the present disclosure.

In the embodiments of FIGS. 3 and 4, the analytical power was determined to be approximately 6.3 mW (481 mA current), power stabilization time was around 3 minutes, and, for Raman spectrum acquisition, the CCD (Charge Coupled Device) detector integration time was about 4 seconds and the detector data were read in a single reading operation. An exemplary detector-based spectroscopy system 105 is illustrated in FIG. 10 and discussed later hereinbelow.

Figure 5:
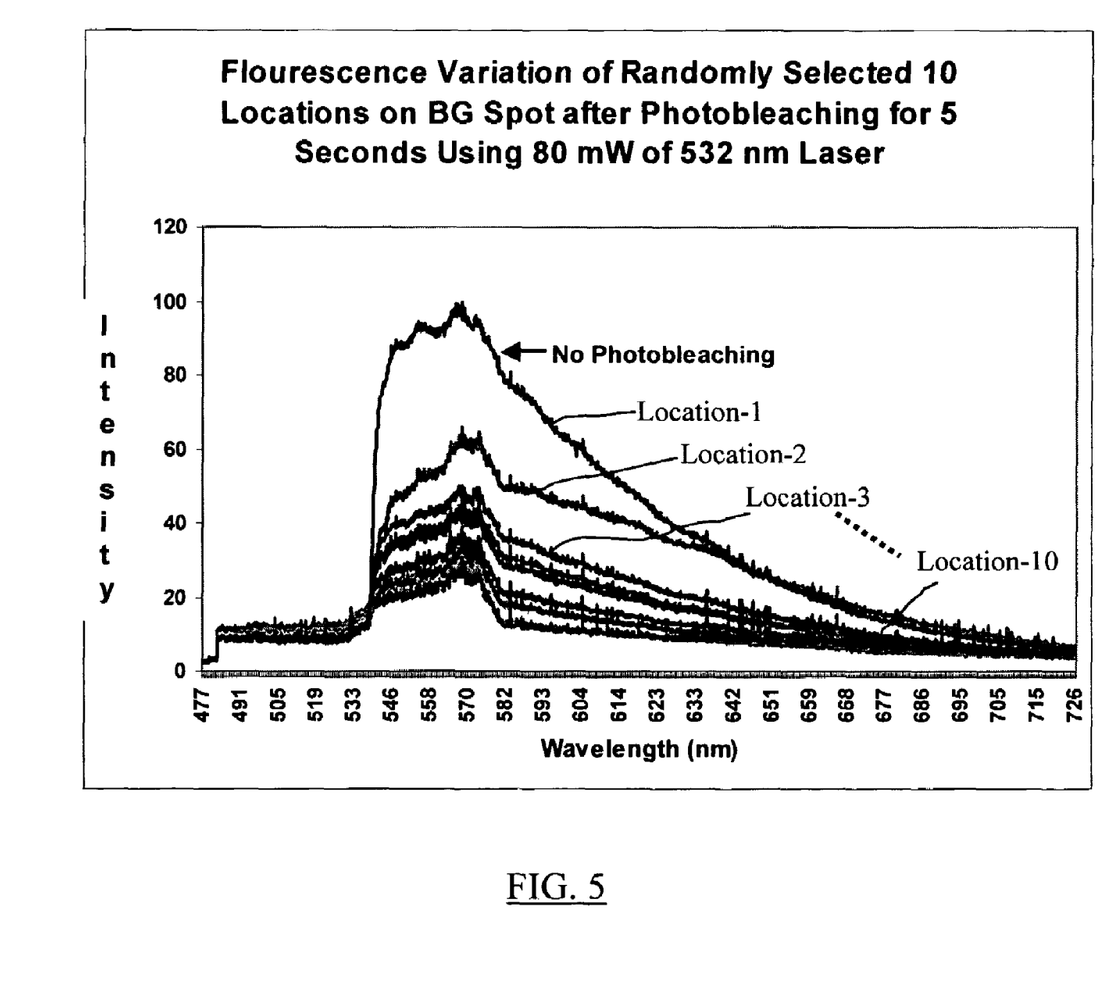
FIG. 5 illustrates spatial variations in fluorescence at randomly selected ten spatial locations on a Bg sample after nine of the ten locations on the Bg sample were photobleached for 5 seconds using a 532 nm laser at the photobleaching power level as per the teachings of one embodiment of the present disclosure.

FIG. 5 illustrates spatial variations in fluorescence (as opposed to the temporal variations at a single location in the MCC sample of FIG. 7 discussed below or at two Bg locations in FIGS. 3A and 4A discussed above) at randomly selected ten (10) spatial locations on a Bg sample after nine of the ten locations on the Bg sample were photobleached for about 5 seconds using a 532 nm laser at about 80 mW of laser power (i.e., the photobleaching power level in this embodiment) as per the teachings of one embodiment of the present disclosure. The fluorescence curve for the non-photobleached location (i.e., Location-1 in FIG. 5) after the 5 second interval is also shown for comparison to show that the photobleaching at higher laser intensity (i.e., at the photobleaching power level) can reduce the fluorescence anywhere between about 35% to 70% of the non-photobleached level depending on the sample location. Because of such spatial variations in residual fluorescence, it may be possible to select a spatial location on the sample that has significantly reduced fluorescence after a short period of photobleaching so as not to expend time and laser power on further photobleaching efforts. FIG. 5 thus illustrates that such selection is possible when the sample has spatial variations in fluorescence (i.e., when the fluorescence emission is not uniform throughout the sample) and when a few adjacent locations on a sample are photobleached at higher laser intensity (i.e., at the photobleaching power level according to the teachings of one embodiment of the present disclosure) to quickly narrow the choice to one or two locations from where the Raman spectra (or any other spectral data) can be collected at a significantly lower laser power (e.g., at the analytical power level discussed hereinbelow).

In the embodiment of FIG. 5, the laser operating temperature was 5.3 kOhms, the laser wavelength was 532 nm, the analytical power was determined to be approximately 6.3 mW (481 mA current), and the photobleaching power was approximately 80 mW (814 mA current). The laser power stabilization time was approximately 3 to 5 minutes. However, it was observed that within the first three minutes after changing the current (from 814 mA to 481 mA), the variation in laser power was approximately 5%, but was less than 1% after about 3 minutes have elapsed. In the embodiment of FIG. 5, the power was considered stabilized 3 minutes after the current was changed from the higher level (for photobleaching) to the lower level (for Raman or other spectroscopic measurements). In case of the Bg sample of FIG. 5, for Raman spectrum acquisition, the CCD detector integration time was approximately 6 seconds and the detector data were read in a single reading operation. As noted before, a detector-based spectroscopic system similar to the exemplary system 105 illustrated in FIG. 10 may be used for Raman spectrum acquisition.

Figure 6:
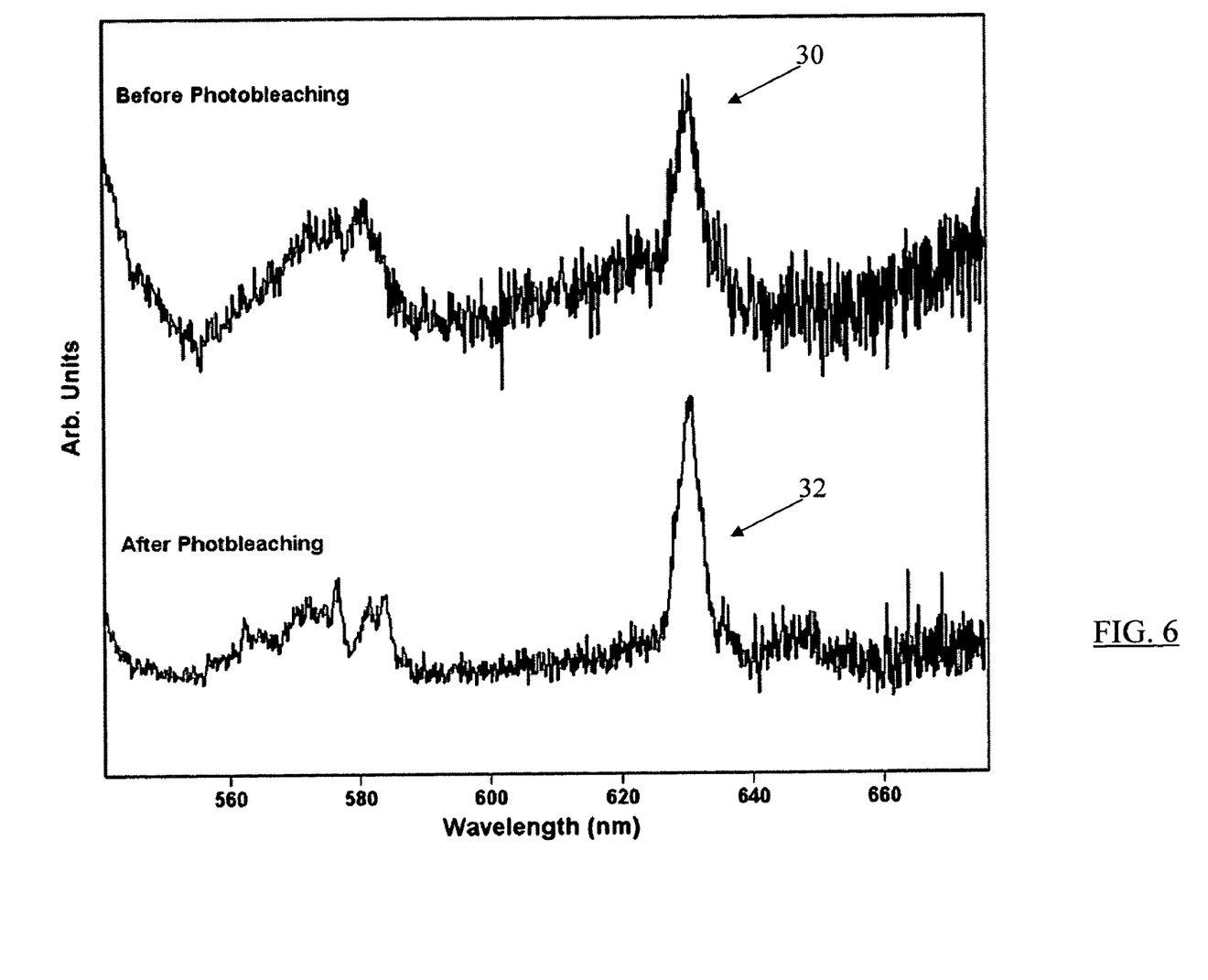
FIG. 6 illustrates two exemplary plots—a pre-photobleaching plot and a post-photobleaching plot—obtained for a Bt sample location according to one embodiment of the present disclosure.

FIG. 6 illustrates two exemplary plots—a pre-photobleaching plot 30 and a post-photobleaching plot 32—obtained for a Bt sample location according to one embodiment of the present disclosure. The first plot 30 depicts a Raman spectrum obtained when the sample location (on the Bt sample) is not photobleached, whereas the second plot 32 shows the Raman spectrum when the sample location is photobleached (at photobleaching power) according to the teachings of one embodiment of the present disclosure. Both photobleached and non-photobleached spectra 30, 32 were processed to remove bias, dark current, and background (which may be removed through a background subtraction process). It is seen from FIG. 6 that the photobleached plot 32 depicts sharper Raman peaks and a cleaner wave shape as opposed to the non-photobleached version 30. The notation "Arb. Units" along the y-axis for the plots in FIG. 6 is a shorthand for "arbitrary units" of spectral intensity.

Figure 7A:
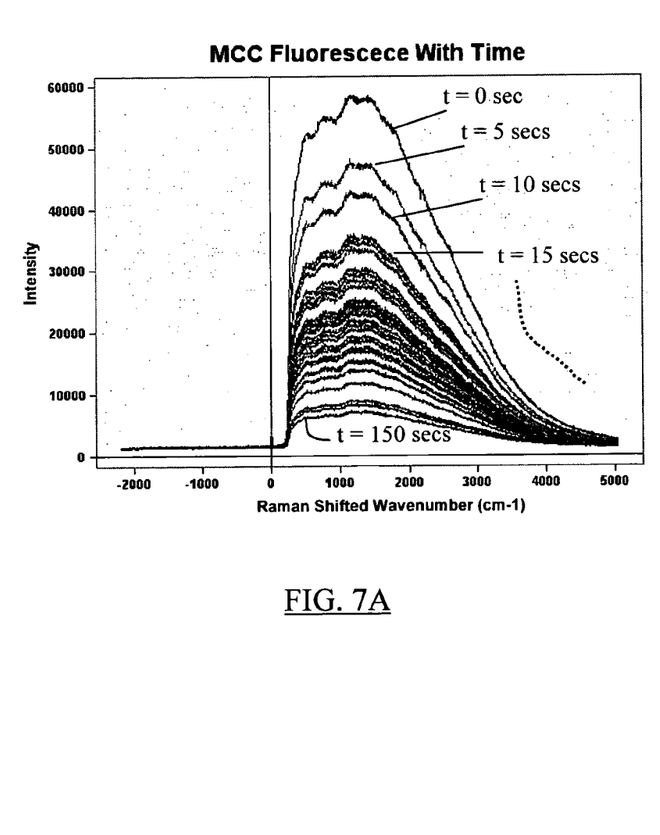
FIG. 7A is an exemplary set of plots depicting fluorescence decay with time at a single location in an MCC sample, whereas the plot in FIG. 7B shows corresponding photobleach rate when the MCC sample location is photobleached according to the teachings of one embodiment of the present disclosure.
Figure 7B:
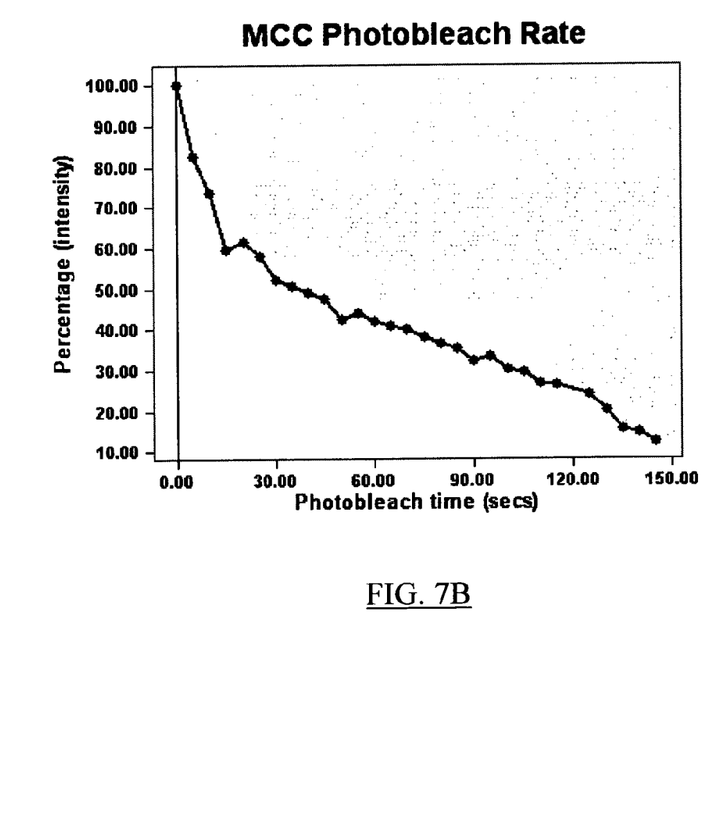

FIG. 7A is an exemplary set of plots depicting fluorescence decay with time at a single location in an MCC sample, whereas the plot in FIG. 7B shows corresponding photobleach rate when the MCC sample location is photobleached according to the teachings of one embodiment of the present disclosure. Some exemplary time values indicated on the plots in FIG. 7A correspond to the photobleach time (in seconds) represented on the x-axis in the plot in FIG. 7B. It is observed from various plots in FIG. 7A that the native fluorescence (the top-most curve in FIG. 7A at t=0 sec) may substantially reduce over time so as not to interfere with subsequent spectroscopic (e.g., Raman) measurements. The plot in FIG. 7B depicts the photobleach rate when the location of the MCC sample is photobleached using a 532 nm laser with approximately 70 mW of power at 5.3 kOhms temperature (700 mA current drive). This 70 mW power may be considered the photobleaching power level in case of this MCC sample. On the other hand, the analytical power (e.g., for Raman spectrum measurements) for this MCC sample location was determined to be about 4 mW (400 mA current). For Raman spectrum acquisition from this MCC sample, the CCD detector integration time was about 1 second and the detector data were read in a single reading operation. It is seen from the plot in FIG. 7B that the significantly higher power level for photobleaching resulted in reduction in fluorescence from its initial level to the 10% of the initial level in about 150 seconds. Depending on the desired reduction in fluorescence, the photobleaching may be stopped when, for example, the fluorescence has been bleached to about 25% of its initial level, or to 15% of its initial level, etc., so long as there is acceptable stabilization in the FOM as discussed hereinbefore. In one embodiment, the Raman spectrum measurements may then start at the lower laser power (the "analytical power") as discussed hereinbefore.

For the MCC sample plots in the embodiment of FIG. 7: (1) The analytical power level was determined by using a non-photobleached location in the sample and finding a highest laser power level (by illuminating the non-photobleached sample location with varying power levels) at which the optical detector (e.g., a CCD detector) (not shown) of the spectroscopic instrument examining the MCC sample did not get saturated. This power level was treated as the analytical power. In another embodiment, a different power level (other than the highest power level) that does not saturate the detector may also be used as the analytical power level for the sample under investigation. (2) Thereafter, the laser illumination was applied to the non-photobleached location with power significantly higher than the analytical power, but lower than the MCC sample's photodamage threshold. The higher laser power (i.e., the photobleaching power) was applied for a given time (i.e., until the FOM didn't change significantly as discussed hereinbefore) to reduce the native luminescence from the sample location. (3) The sample location was now sufficiently photobleached and, hence, laser illumination with analytical power was applied to this photobleached location to acquire a Raman spectrum for the sample.

Thus, in one embodiment, the photobleaching power may be related to the analytical power by some percentage (>100%), which may depend on various factors including, for example, the material to be photobleached. For example, in case of the Bg sample in the embodiments of FIGS. 3 and 4, the photobleaching power (approximately 80 mW) is about 12.7 times (i.e., about 1270%) the analytical power (approximately 6.3 mW). On the other hand, in case of the MCC sample in the embodiment of FIG. 7, the photobleaching power (approximately 70 mW) is about 17.5 times (i.e., about 1750%) the analytical power (approximately 4 mW). Thus, the following equation may be used to generally represent the variable relationship between the photobleaching power ($P_P$) and the analytical power ($P_A$):

$$P_P = (1+X)P_A, \text{ wherein } X \geq 0 \quad (1)$$

In the equation (1) above, for example, when X=0.5, the photobleaching power is 150% of the analytical power; when X=1, the photobleaching power is twice (200%) the analytical power; and so on.

Figure 8:
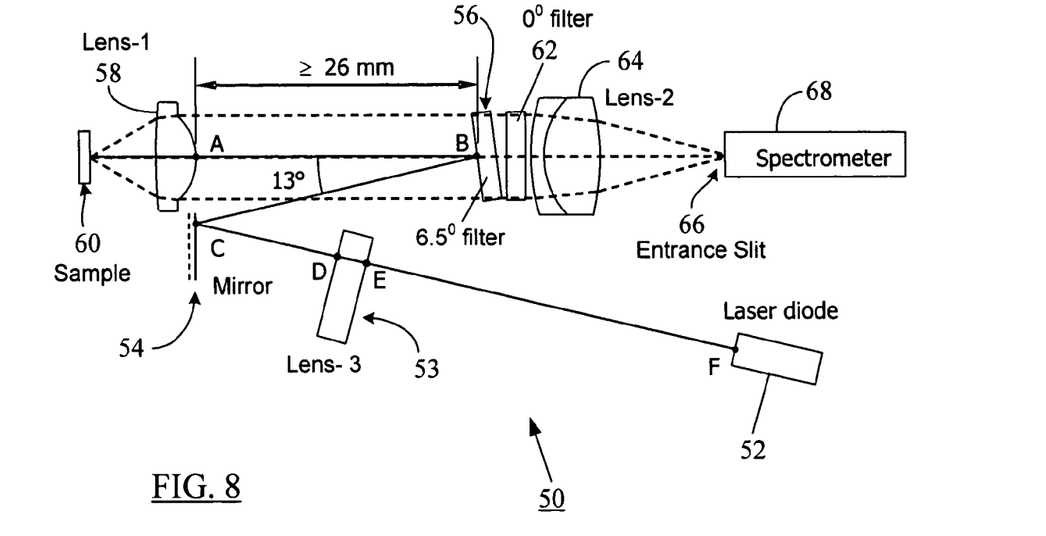
FIG. 8 illustrates a schematic of an exemplary, single laser-based Raman spectroscopy system that may be configured to perform the pulse photobleaching according to the teachings of one embodiment of the present disclosure.

FIG. 8 illustrates a schematic of an exemplary, single laser-based Raman spectroscopy system 50 that may be configured to perform the pulse photobleaching according to the teachings of the present disclosure. The system 50 may be used for portable or handheld applications in the field to detect, for example, hazardous biothreat (e.g., anthrax) or chemical agents (e.g., ricine or other poison) using principles of Raman spectroscopy. The excitation or illumination source in the system 50 includes a single laser 52, which, as mentioned hereinbefore, may be either a dual-intensity software controlled CW laser or a fixed intensity CW laser used in conjunction with a neutral density filter (not shown). In the embodiment of FIG. 8, the laser diode 52 may be used to provide an oblique illumination onto a mirror 54. The laser illumination reflected from the mirror 54 is then focused onto a sample 60 under investigation using a combination of a longpass filter 56 and a focusing lens (Lens-1) 58. The longpass filter 56 serves to reflect the incident laser light towards Lens-1 during sample illumination, and to pass all Raman scattered light received from the sample 60 to a collecting lens 64 (Lens-2) during the Raman signal collection phase. An additional lens 53 may be placed between the laser diode 52 and the mirror 54 to manipulate the shape or size of the laser illumination on the sample 20. Thus, in the embodiment of FIG. 8, all laser illumination (whether at photobleaching power level or at analytical power level) travels along the path indicated by reference letters "FEDCBA" and is applied substantially at right angle to the sample surface. In other embodiments, alternative illumination arrangements may be devised in which illuminating photons arrive at the sample location in directions other than a vertical or right-angle orientation with reference to the sample surface being illuminated.

In the system 50 of FIG. 8, the Raman scattered light from the sample 60 is initially collected by focusing lens 58, "cleaned" by the 6.5° longpass filter 56 (which blocks some photons having the illuminating laser wavelength) and a 0° filter 62 (which is a laser line rejection filter that further blocks photons having the illuminating laser wavelength), and then focused onto an entrance slit 66 of a spectrometer 68 by the collecting lens (Lens-2) 64. In FIG. 8, the laser illumination path (identified by reference letters "FEDCBA") is indicated by a solid line whereas the propagation of Raman scattered light is indicated by the dotted lines. The spectrometer 68 may be a gratings-based dispersive spectrometer, which may measure the Raman spectrum of the sample 60 using the photons received at its entrance slit 66 and provide further spectral analysis of the sample 60 as selected by a user of the portable spectroscopy system 50. Various components in the system 50 in FIG. 8 and their functionalities are known to one skilled in the art, and, hence, a detailed description of the system 50 is not provided herein. It is noted here that the embodiment in FIG. 8 is for illustration only; any other optical or chemical imaging system may be suitably adapted to carry out the pulse photobleaching as per discussion provided herein.

In the Raman spectroscopy system 50 in FIG. 8, an exemplary spatial relationship among various components in the system is also illustrated. For example, a minimum separation of 26 mm may be desirable between the focusing lens 58 and the first filter (i.e., the 6.5° longpass filter 56) so as to maintain a predetermined 13° angle of incidence of illumination light beam BC and its proper reflection by the longpass filter 56 along the lens axis AB.

Figure 9:
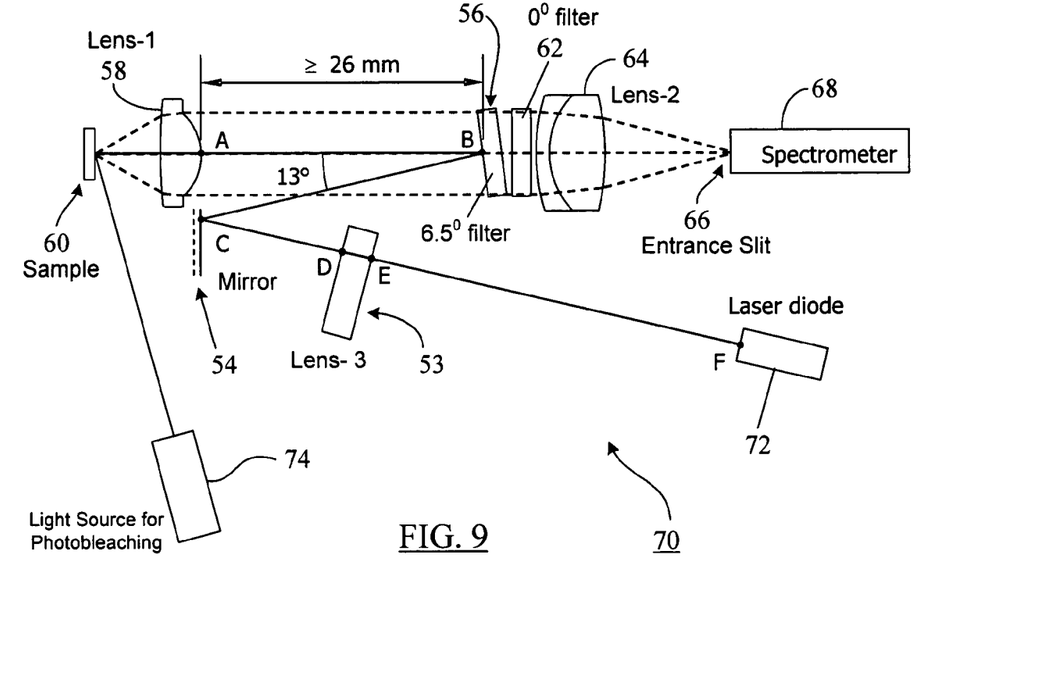
FIG. 9 shows a schematic of an exemplary, dual laser-based Raman spectroscopy system that may be configured to perform the pulse photobleaching according to the teachings of one embodiment of the present disclosure.

In the system 50 in FIG. 8, it is seen that the illumination path for photobleaching as well as photon collection path for Raman data acquisition are the same—i.e., the laser beam "AB" directed substantially perpendicular to the sample surface for both of the applications. However, as mentioned before, such common illumination path may not be necessary as indicated in FIG. 9, which shows a schematic of an exemplary, dual laser-based Raman spectroscopy system 70 that may be configured to perform the pulse photobleaching according to the teachings of one embodiment of the present disclosure. The system 70 in FIG. 9 includes an excitation or illumination source comprised of two separate monochromatic light sources 72 and 74, each may have same or different illumination wavelengths, but may provide different illumination powers. In comparison with the system 50 in FIG. 8, in the system 70 of FIG. 9, a second monochromatic light source (e.g., a UV (Ultra Violet) LED (Light Emitting Diode)) 74 may be used to obliquely illuminate the sample for photobleaching at the higher intensity (i.e., at the photobleaching power level), whereas a laser diode 72 may then be turned on to illuminate the sample with a laser beam directed substantially perpendicular to the sample surface and at a lower (analytical) power level. The Raman scattered photons are then collected using the illumination from this laser diode 72. Thus, the photobleaching and Raman data acquisition may be carried out over two different optical paths. As noted before, each of the two illumination sources 72 74 may have different power ratings—the light source 74 for photobleaching may be capable of providing illumination at a higher power level than the laser diode 72 used for Raman data collection. Furthermore, none of the illumination sources 72 and 74 needs to be an expensive laser having, for example, software-controlled variable intensity. Also, if high power intensities for short durations are found to be effective, the UV light source 74 can be pulsed in temporal increments until the material's luminescence is reduced to a level suitable for the subsequent detection of Raman scattered light. In one embodiment, the UV LED 74 for photobleaching may be a 385 nm UV-LED, rated at 85 mW and marketed by Nichia America Corporation of Mountville, Pa., USA. The laser diode 72 may be a 532 nm laser rated at 150 mW and marketed by Snake Creek Lasers of Hallstead, Pa., USA.

Except for the configuration of the excitation source (one laser based in system 50 vs. two laser based in system 70), there is substantial similarity between the embodiments in FIGS. 8 and 9. Therefore, for the sake of brevity and ease of illustration, components having substantially similar functions in the systems 50 and 70 are identified by similar reference numerals and discussion of such components, which is already provided hereinbefore in conjunction with discussion of FIG. 8, is not repeated in conjunction with discussion of FIG. 9.

FIG. 10 depicts an exemplary compact Raman and/or fluorescence spectroscopy system 105 for portable or handheld spectroscopy applications according to one embodiment of the present disclosure. The system 105 may comprise either of the systems 50 or 70 as per the teachings of one embodiment of the present disclosure. The system 105 may include an illumination source and focusing optics 110 that provides illuminating photons to a sample 112. As mentioned before, the illumination source 110 may include a single laser diode (e.g., the laser diode 52 in the embodiment of FIG. 8) or a combination of two monochromatic light sources (e.g., the laser diode 72 and the LED 74 in the embodiment of FIG. 9) to provide variable illumination—at photobleaching power level and also at analytical power level—as per the teachings of one embodiment of the present disclosure. In one embodiment, the focusing optics 110 may include a single lens or a combination of two or more lenses and other optical elements (e.g., the combination of lens 53, mirror 54, filter 56, and lens 58 in the embodiment of FIG. 8).

When a sample 112 is placed at a focusing location of the focusing optics, the illuminating (or excitation) photons from the illumination source are directed onto the sample 112. The sample 112 may interact with the illuminating photons to provide reflected, scattered, or emitted photons, which photons may be initially collected by the focusing optics 110 and transferred to a photon collection optics 114. In one embodiment, the photon collection optics 114 may include another lens assembly either alone or in combination with a laser line rejection filter (e.g., the rejection filters 56 and 62 in combination with the collection lens 64 as shown in the embodiment of FIG. 8). The photon collection optics 114 may direct the Raman scattered or fluorescence (emitted) photons received from the sample to a spectral selection unit 116, which may be a dispersive (e.g., gratings-based) spectrometer or an optical tunable filter (e.g., an electronically tunable liquid crystal tunable filter (not shown)). An exemplary dispersive spectrometer based embodiment is illustrated in FIG. 8. The spectrometer in the spectral selection unit 116 may generate a spectrum of the sample 112 under investigation over a selected spectral range of interest. In one embodiment, the compact spectroscopy unit 105 may include a detector 118 optically coupled to the spectrometer or tunable filter 116 to generate data that can be used to display a spectral image of the sample 112. The detector 118 may receive an optical output (e.g., a wavelength-dispersed optical signal in case of a dispersive spectrometer or a wavelength-specific spectral output in case of a liquid crystal-based tunable filter) from the spectral selection unit 116 and generate signal data therefrom. The signal data may be supplied to an electronic display unit 120 to display a wavelength-specific spectral image of the sample 112 under investigation. In one embodiment, the detector 118 may a part of a spectrometer unit, in which case, the spectrometer at block 116 may include the functionality of the detector 118. In one embodiment, the detector 118 may be a charge coupled device (CCD). In another embodiment, the detector 118 may be a complementary metal oxide semiconductor (CMOS) array. In an alternative embodiment, the display unit 120 may be a computer display screen, a display monitor, or a small LCD (liquid crystal display) screen.

The compact spectroscopy system 105 may also include a programmable control unit 122, which can be suitably programmed to electronically control functionalities of one or more of the system elements including, for example, the illumination source and focusing optics 110, the collection optics 114, the spectral selection unit 116, the detector 118, and the display unit 120 as shown by the exemplary illustration in FIG. 10. The control unit 122 may be a computing or data processing unit that can be suitably programmed for collecting and processing spectral information from the samples under investigation. Thus, in one embodiment, the control unit 122 may be configured to store values of photodamage thresholds of a number of samples that may be encountered in the field. Furthermore, in another embodiment, the control unit 122 may be configured to compute one or more figures-of-merit (FOM's) to guide the photobleaching process as discussed hereinbefore. The control unit 122 may include electronic memory (not shown) to store different types of data and information (e.g., spectroscopic data, time values for photobleaching or optical response measurements, etc.) so as to assist an operator in substantially automating various operational aspects including, for example, the photobleaching and spectral data collection aspects.

It is noted that although discussion herein primarily focuses on spectroscopic systems employing the teachings of the present disclosure to collect Raman spectra or images of luminescent materials, it may be evident to one skilled in the art that the teachings of the present disclosure can be used along with any other non-Raman spectroscopic measurement, chemical imaging, or data collection techniques. Furthermore, as noted before, the pulse photobleaching methodology according to the teachings of the present disclosure may also be used in stand-alone photobleaching applications without any spectral measurement or chemical imaging aspect. Also, even if exemplary portable spectroscopic systems are shown in FIGS. 8 and 9, it is further evident to one skilled in the art that the teachings of the present disclosure could be used with any type of spectroscopic or non-spectroscopic systems—portable or stationary.

The foregoing describes various embodiments of a pulse photobleaching methodology wherein a monochromatic illumination (e.g., laser illumination) having a higher power intensity (photobleaching power) just below the photodamage threshold of a luminescent sample is initially used to significantly attenuate sample luminescence without photothermally destroying the sample material. Thereafter, the laser power density may be reduced to a significantly lower level (analytical power level) to carry out spectroscopic measurements (e.g., collection of Raman scattered photons) on the sample. In one embodiment, the laser illumination wavelength remains the same despite changes in laser power intensity. Some figures-of-merit may be computed from optical measurements made at the analytical power level to guide the photobleaching process. Sample-dependent combinations of laser power density and short exposure times may be obtained to significantly expedite photobleaching to assist in collection of sample spectral data in the field without a long wait. Portable spectroscopy systems employing pulse photobleaching may be devised for expeditious collection of spectral data from luminescent samples in the field.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A method comprising:
photobleaching a sample by applying a monochromatic illumination at a first intensity level to said sample for a first duration, wherein said first intensity level is slightly lower than a photodamage threshold of said sample;
reducing intensity of said illumination from said first intensity level to a second intensity level without changing wavelength of said illumination, wherein said second intensity level is substantially lower than said first intensity level; and
applying said illumination at said second intensity level to said sample for a second duration so as to measure an optical response of said sample, wherein said optical response includes a Raman spectrum of the sample.

2. A method comprising:
photobleaching a sample by applying a monochromatic illumination at a first intensity level to said sample for a first duration, wherein said first intensity level is slightly lower than a photodamage threshold of said sample;
reducing intensity of said illumination from said first intensity level to a second intensity level without changing wavelength of said illumination, wherein said second intensity level is substantially lower than said first intensity level;
applying said illumination at said second intensity level to said sample for a second duration so as to measure an optical response of said sample;
computing a figure-of-merit (FOM) from said optical response;
repeating said photobleaching, said applying, and said computing steps until a most recently computed figure-of-merit is within a predetermined range of an immediately previously computed figure-of-merit; and
after said repeating is over, performing an optical spectroscopic measurement on said sample using said illumination only at said second intensity level.

3. The method of claim 2, wherein performing said optical spectroscopic measurement includes collecting a Raman spectrum of the sample.

4. The method of claim 2, wherein said FOM includes one or more of the following: a first computation of total intensity of a first plurality of points on a fluorescence spectrum obtained through measurement of said optical response; a second computation of sum of square of intensities of a second plurality of points on said fluorescence spectrum; a first detection of lack of saturation in said fluorescence spectrum; and a second detection of presence of a CH peak in said fluorescence spectrum.

5. The method of claim 2, wherein said predetermined range is about 2% to 5% above an optical detector readout variation.

6. A method comprising:
photobleaching a sample by applying a monochromatic illumination at a first intensity level to said sample for a first duration, wherein said first intensity level is slightly lower than a photodamage threshold of said sample;
reducing intensity of said illumination from said first intensity level to a second intensity level without changing wavelength of said illumination, wherein said second intensity level is substantially lower than said first intensity level; and
applying said illumination at said second intensity level to said sample for a second duration so as to measure an optical response of said sample, wherein determining said second intensity level by is determined by:
applying said illumination to a non-photobleached location on the sample;
varying intensity levels of said illumination applied to said non-photobleached location and detecting light emitted or scattered from said non-photobleached location at each varied intensity level using an optical detector; and
identifying a highest intensity level that fails to saturate said optical detector during said varying as said second intensity level.

7. A method comprising:
photobleaching a sample by applying a monochromatic illumination at a first intensity level to said sample for a first duration, wherein said first intensity level is slightly lower than a photodamage threshold of said sample, wherein said photodamage threshold is a pre-determined value for said photodamage threshold:
storing said pre-determined value in an electronic memory prior to said photobleaching:
reducing intensity of said illumination from said first intensity level to a second intensity level without changing wavelength of said illumination, wherein said second intensity level is substantially lower than said first intensity level; and
applying said illumination at said second intensity level to said sample for a second duration so as to measure an optical response of said sample.

8. A method comprising:
photobleaching a sample by applying a monochromatic illumination at a first intensity level to said sample for a first duration, wherein said first intensity level is slightly lower than a photodamage threshold of said sample;
determining a value for said photodamage threshold at run time prior to commencing said photobleaching:
reducing intensity of said illumination from said first intensity level to a second intensity level without changing wavelength of said illumination, wherein said second intensity level is substantially lower than said first intensity level; and
applying said illumination at said second intensity level to said sample for a second duration so as to measure an optical response of said sample.

9. A system comprising:
a sample; and
an excitation source configured to illuminate said sample using monochromatic light, wherein said excitation source is configured to provide the following:
a first illumination having a first intensity level and configured to be applied to said sample for a first duration so as to photobleach said sample, wherein said first intensity level is slightly lower than a photodamage threshold of said sample, and
a second illumination identical in wavelength to said first illumination and having a second intensity level, wherein
said second intensity level is substantially lower than said first intensity level,
said second illumination is configured to be applied to said sample after said first illumination for a second duration so as to measure an optical response of said sample, and
wherein said first and said second illuminations are configured to be applied to said sample along different optical paths.

10. A system comprising:
a sample;
an excitation source configured to illuminate said sample using monochromatic light, wherein said excitation source is configured to provide the following:
  a first illumination having a first intensity level and configured to be applied to said sample for a first duration so as to photobleach said sample, wherein said first intensity level is slightly lower than a photodamage threshold of said sample, and
  a second illumination identical in wavelength to said first illumination and having a second intensity level, wherein said second intensity level is substantially lower than said first intensity level, and wherein said second illumination is configured to be applied to said sample after said first illumination for a second duration so as to measure an optical response of said sample;
a collection optics to collect photons scattered, reflected, or emitted from said sample when said sample is illuminated by said second illumination, wherein said collection optics includes: an optical filter for receiving photons emitted, scattered, or reflected from said sample and for generating filtered photons therefrom, wherein said filtered photons include those of the photons received from the sample that have wavelengths other than the wavelength of said second illumination; and a collection lens coupled to said optical filter for sending said filtered photons received from the optical filter to the spectral analysis system; and
a spectral analysis system coupled to said collection optics to receive a portion of said collected photons therefrom and to responsively measure a spectrum of said sample using said portion of said collected photons.

11. A system comprising:
a sample;
an excitation source configured to illuminate said sample using monochromatic light, wherein said excitation source is configured to provide the following:
  a first illumination having a first intensity level and configured to be applied to said sample for a first duration so as to photobleach said sample, wherein said first intensity level is slightly lower than a photodamage threshold of said sample, and
  a second illumination identical in wavelength to said first illumination and having a second intensity level, wherein said second intensity level is substantially lower than said first intensity level, and wherein said second illumination is configured to be applied to said sample after said first illumination for a second duration so as to measure an optical response of said sample;
a collection optics to collect photons scattered, reflected, or emitted from said sample when said sample is illuminated by said second illumination; and
a spectral analysis system coupled to said collection optics to receive a portion of said collected photons therefrom and to responsively measure a spectrum of said sample using said portion of said collected photons, wherein said spectral analysis system includes a dispersive spectrometer that comprises: an entrance slit to receive said portion of said collected photons from said collection optics; and a plurality of gratings to provide wavelength-specific dispersion of said portion of said collected photons received at the entrance slit so as to measure said spectrum of said sample.

12. A system comprising:
a sample;
an excitation source configured to illuminate said sample using monochromatic light, wherein said excitation source is configured to provide the following:
  a first illumination having a first intensity level and configured to be applied to said sample for a first duration so as to photobleach said sample, wherein said first intensity level is slightly lower than a photodamage threshold of said sample, and
  a second illumination identical in wavelength to said first illumination and having a second intensity level, wherein said second intensity level is substantially lower than said first intensity level, and wherein said second illumination is configured to be applied to said sample after said first illumination for a second duration so as to measure an optical response of said sample
a collection optics to collect photons scattered, reflected, or emitted from said sample when said sample is illuminated by said second illumination;
a spectral analysis system coupled to said collection optics to receive a portion of said collected photons therefrom and to responsively measure a spectrum of said sample using said portion of said collected photons; and
a detector optically coupled to said spectral analysis system to receive an output signal therefrom and to responsively provide optical data to generate a wavelength-specific spectral image of said sample.

13. The system of claim 12, wherein the detector is one of the following: a charged coupled device (CCD), and a complementary metal oxide semiconductor (CMOS) array.

14. A system comprising:
a sample;
an excitation source configured to illuminate said sample using monochromatic light, wherein said excitation source is configured to provide the following:
  a first illumination having a first intensity level and configured to be applied to said sample for a first duration so as to photobleach said sample, wherein said first intensity level is slightly lower than a photodamage threshold of said sample, and
  a second illumination identical in wavelength to said first illumination and having a second intensity level, wherein said second intensity level is substantially lower than said first intensity level, and wherein said second illumination is configured to be applied to said sample after said first illumination for a second duration so as to measure an optical response of said sample; and
an optical filter for receiving photons emitted, scattered, or reflected from said sample when said sample is illuminated by said second illumination and for generating a first set of filtered photons therefrom, wherein said first set of filtered photons includes those of the photons received from the sample that have wavelengths other than the wavelength of said second illumination; a liquid crystal-based tunable filter to receive said first set of filtered photons from said optical filter and to generate a second set of filtered photons therefrom, wherein said second set of filtered photons include only those photons from said first set of filtered photons that have a wavelength to which said tunable filter is tuned; a collection lens coupled to said tunable filter for sending said second set of filtered photons received from the tunable filter to a detector; and said detector coupled to said collection lens to receive said second set of filtered photons therefrom and to responsively provide optical data to generate a wavelength-specific spectral image of said sample at the wavelength to which said tunable filter is tuned.

15. A system comprising:

means for applying a laser illumination to a luminescent sample at a first intensity level and for a first duration so as to photobleach said sample, wherein said first intensity level is slightly lower than a photodamage threshold of said sample;

means for applying said laser illumination to said sample at a second intensity level and for a second duration after said first duration without changing wavelength of said illumination, wherein said second intensity level is substantially lower than said first intensity level; and means for measuring a spectral response of said sample when said laser illumination is applied to said sample at said second intensity level.

16. The system of claim 15, wherein said means for measuring said spectral response includes means for measuring a Raman spectrum of said sample from photons scattered from said sample in response to said laser illumination at said second intensity level.

* * * * *